United States Patent [19]

Schneider et al.

[11] Patent Number: 4,707,242

[45] Date of Patent: Nov. 17, 1987

[54] ELECTROCHEMICAL CELL FOR THE DETECTION OF NOXIOUS GASES

[75] Inventors: Alan A. Schneider, Reisterstown; David A. Stewart; Joseph D. Jolson, both of Baltimore; RaeAnn M. Auel, Westminster; John F. Price, Owings Mill, all of Md.

[73] Assignee: Mine Safety Appliances Company, Pittsburgh, Pa.

[21] Appl. No.: 760,144

[22] Filed: Jul. 29, 1985

Related U.S. Application Data

[63] Continuation-in-part of Ser. No. 646,316, Aug. 30, 1984.

[51] Int. Cl.⁴ .................................... G01N 27/46
[52] U.S. Cl. .................................... 204/412; 204/1 T; 204/402; 204/432; 204/435
[58] Field of Search ............... 204/1 P, 1 T, 400, 412, 204/415, 432, 433, 435, 402

[56] References Cited

U.S. PATENT DOCUMENTS

| | | | |
|---|---|---|---|
| 2,805,191 | 9/1957 | Hersch | 204/1 Y |
| 3,235,477 | 2/1966 | Keyeser et al. | 204/415 |
| 3,454,485 | 7/1969 | Hahk et al. | 204/415 |
| 3,503,861 | 3/1970 | Volpe | 204/415 |
| 3,510,421 | 5/1970 | Gealt | 204/415 |
| 3,824,167 | 7/1974 | Oswin et al. | 204/1 K |
| 4,100,048 | 7/1978 | Pompei et al. | 204/415 |
| 4,169,779 | 10/1979 | Tataria et al. | 204/415 |
| 4,324,257 | 4/1982 | Albarda et al. | 204/415 |
| 4,377,446 | 3/1983 | Albery | 204/415 |
| 4,406,770 | 9/1983 | Chan et al. | 204/415 |
| 4,507,194 | 3/1985 | Shimomura et al. | 204/435 |

FOREIGN PATENT DOCUMENTS 2073891 10/1981 United Kingdom ............... 204/415

OTHER PUBLICATIONS

Lingane, *Electroanalytical Chemistry*, 2d.ed., revised, 1958, p. 28.

Primary Examiner—T. Tung
Attorney, Agent, or Firm—Reed Smith Shaw & McClay

[57] ABSTRACT

The present invention is for an electrochemical cell and method for quantitatively detecting noxious gas which comprises a first working electrode comprising a gas diffusion membrane having bonded thereto a catalytic portion electrochemically reactive with the noxious gas; a second working electrode having electrochemical activity with the oxidation/reduction products produced at the first working electrode; a counter electrode; a reference electrode; an electrolyte; means for containing said electrolyte and said electrodes; means for maintaining a fixed potential on said first working electrode relative to said reference electrode of from about 1.0 to 1.8 volts with respect to the potential of the reversible hydrogen couple of the electrolyte of the cell; and means for maintaining a fixed potential on said second working electrode relative to said reference electrode of from about 1.0 to 2.2 volts with respect to the potential of the reversible hydrogen couple of the electrolyte of the cell, the fixed potential on said working electrode being maintained at a voltage higher than the fixed potential being maintained on said first working electrode.

19 Claims, 6 Drawing Figures

ELECTROCHEMICAL CELL FOR THE DETECTION OF NOXIOUS GASES

CROSS-REFERENCE TO OTHER APPLICATIONS

This is a continuation in part of our copending application Ser. No. 06/646,316, filed Aug. 30, 1984.

FIELD OF THE INVENTION

The present invention relates in general to an electrochemical cell for, and a method for, the measurement of noxious gases and in a most preferred embodiment to an electrochemical cell for, and a method for, the measurement of ethylene oxide.

BACKGROUND OF THE INVENTION

Ethylene oxide (EtO) is a commonly used, highly effective, sterilizing gas. Although ethylene oxide is vitally important to health care providers, to manufacturers and sterilizers of medical products and to spice and other food manufacturers, all of which use ethylene oxide as a sterilant, ethylene oxide has been determined to be toxic. Various federal agencies, including the Environmental Protection Agency and the National Institute for Occupational Safety and Health, have recently recommended standards and exposure levels to reduce permissible exposure limits for a worker exposed to or working with ethylene oxide from fifty parts of ethylene oxide per million parts of air during an eight hour period to one part per million parts of air during an eight hour period.

Prior art sensors for the measurement of ethylene oxide and other noxious gases are known, such as photoionization sensors, gas chromatographic sensors and infrared sensors, and are commonly in the form of infrared sensors. See, e.g., Monitoring Ethylene Oxide With Direct Reading Instrumentation by Charles W. Opp, Chapter 7, "The Safe Use of Ethylene Oxide, Proceedings of An Educational Seminar," HEMA Report 80-4, December 1980. However, these prior art ethylene oxide and other noxious gas sensors suffer from a variety of problems, including unacceptable specificity, inability to accurately measure low airborne concentrations, reproducability of measurements, inappropriately long response times, portability problems, short measurement life and high cost.

Electrochemical gas sensors and devices are also well known in the prior art. See, e.g., U.S. Pat. Nos. 4,184,937; 3,992,267; 3,824,167; and 3,776,832. These sensors and devices are used to detect a variety of noxious gases, including hydrogen sulfide, chlorine, nitric oxide, carbon monoxide and various hydrocarbons. However, it is presently believed that no one has successfully developed to date an electrochemical cell for the accurate detection and measurement of ethylene oxide and other noxious gases at levels as low as one part per million and less.

A need, therefore, exists for an electrochemical cell for the continuous measurement of noxious gases, such as ethylene oxide, ethylene glycol, ethanol, acetaldehyde, acetone, isopropanol, propylene oxide and other two to four carbon chain gases, having good selectivity, good sensitivity, the ability to measure airborne levels at one part per million and less, good reproducability, a good measurement life and a reasonable cost.

SUMMARY OF THE INVENTION

The present invention is for an electrochemical cell for quantitatively measuring a noxious gas comprising:

(a) a first working electrode comprising a gas diffusion membrane having bonded thereto a catalytic portion electrochemically reactive with a noxious gas such as ethylene oxide, (b) a second working electrode having electrochemical activity with the oxidation/reduction products produced at the first working electrode (c) a counter electrode, (d) a reference electrode, (e) an electrolyte in contact with the catalytic portion of the first working electrode and in contact with the second working, counter and reference electrodes;

(f) means for containing said electrolyte and said first and second working electrodes, said counter electrode and said reference electrode;

(g) means for maintaining a fixed potential on the first working electrode relative to the reference electrode of from about 1.0 to 1.8 volts with respect to the potential of the reversible hydrogen couple in the electrolyte of the cell; and (h) means for maintaining a fixed potential on said second working electrode relative to said reference electrode of from about 1.0 to 2.2 volts with respect to the potential of the reversible hydrogen couple in the electrolyte of the cell, the fixed potential on said second working electrode being maintained at a voltage higher than the fixed potential being maintained on said first working electrode.

The electrochemical cell, and method, of the present invention is effective for the measurement of noxious gases in general, preferably with noxious gases selected from the group consisting of ethylene oxide, ethylene glycol, acetaldehyde, acetone, ethanol, isopropanol, propylene oxide and other two to four carbon chain gases, and most preferably with ethylene oxide.

In a preferred embodiment of the electrochemical cell of the present invention, each of the first and second working electrodes and the counter electrode comprises a gas diffusion membrane having bonded thereto a catalytic portion selected from the group consisting of palladium, platinum, iridium, ruthenium, rhodium, osmium and alloys and mixtures of these materials with gold.

In a most preferred embodiment of the invention, the catalytic portion of the first and second electrode is iridium, the catalytic portion of the counter electrode is platinum, the reference electrode is a chloranil/graphite electrode coated with an intimate mixture of sodium sulfate and polycarbonate powder or synthetic rubber and the electrolyte is an aqueous sulfuric acid solution.

The invention is further directed to a method for the measurement of noxious gas using the electrochemical cell as further claimed and described hereinabove and hereinafter.

DETAILED DESCRIPTION OF THE INVENTION

The embodiment of the invention described in detail below is a more preferred embodiment of the invention.

Figure 1:
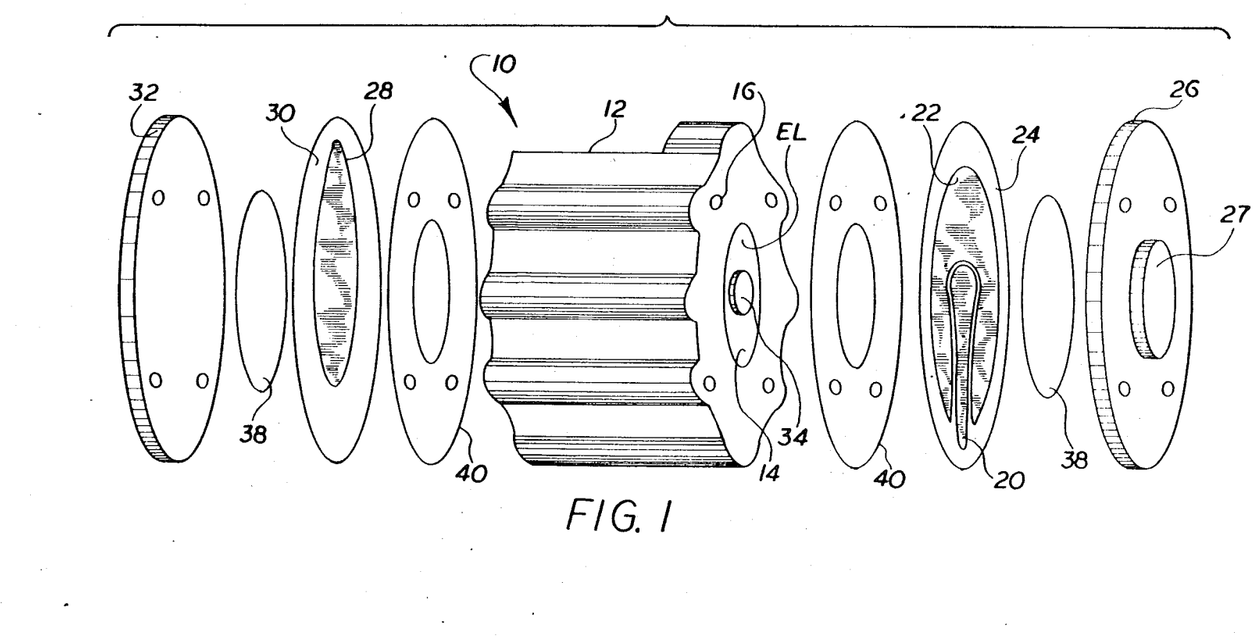
FIG. 1 is a perspective break-away view of an embodiment of the electrochemical cell of the present invention.
Figure 2:
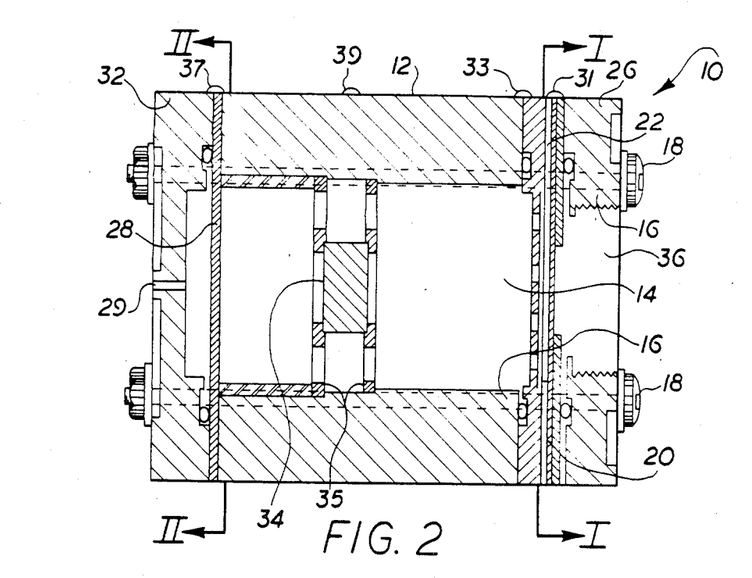
FIG. 2 is a vertical section of the assembled electrochemical cell of the embodiment of the invention set forth in FIG. 1.

Referring to FIGS. 1 and 2, electrochemical cell 10 comprises a housing 12 having a cavity 14 coextensively positioned therethrough. An electrolyte EL is contained within cavity 14 of housing 12. Housing 12 includes openings 16 to receive mounting bolts 18. First working electrode 20 and second working electrode 22 may be mounted on separate porous membranes, but are present, preferably, on a common porous membrane 24 and are sealingly mounted at one end of housing 12 by end plate 26. Counter electrode 28 on porous membrane 30 is sealingly connected to the other end of housing 12 by end plate 32. End plates 26 and 32 are secured to the respective ends of housing 12 by means of mounting bolts 18 (FIG. 2) which pass through openings 16 in housing 12 and correlative openings in end plates 26 and 32 and in membranes 24 and 30. Reference electrode 34 is positioned within cavity 14 by suitable positioning means 35, including wire hangers or a friction-fitting reference electrode holder.

End plate 26 includes gas inlet 27 which is preferably connected to a means for pumping environmental or ambient air into the cell 10 at a closely controlled rate. End plate 26 further includes recess 36 to provide a sufficient area for diffusion of the environmental or ambient air into the membrane of first working electrode 20. End plate 32 contains a pressure relief port 29 through which the environmental or ambient air is vented to the atmosphere if necessary. A variety of "O" rings 38 and gaskets 40 may also be used in conjunction with electrochemical cell 10 to provide desired spacing of the working and counter electrodes 20, 22 and 28 and better sealing of the electrodes and end plates to housing 12.

Figure 5:
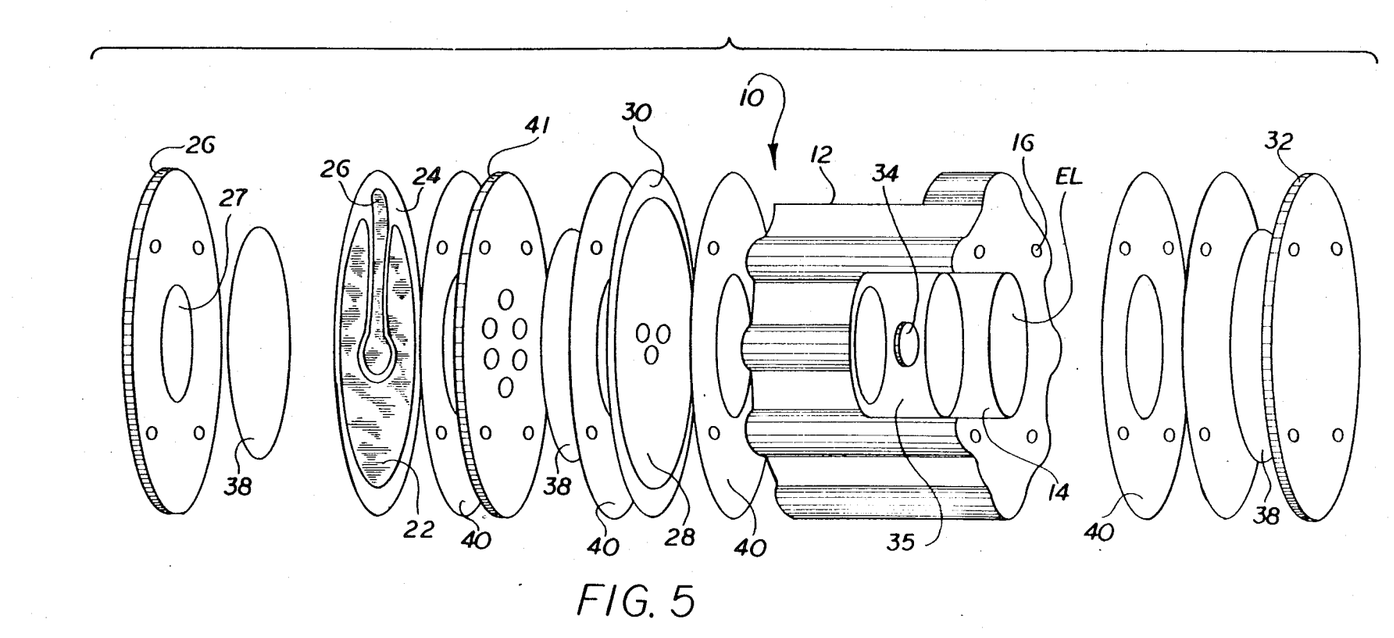
FIG. 5 is a perspective break-away view of a further embodiment of the electrochemical cell of the present invention.

As shown in FIG. 5, in a further embodiment of the electrochemical cell of the invention, counter electrode 28 can be positioned on the same end of housing 12 as first working electrode 20 and second working electrode 22. In such an embodiment, an electrode holder 41 may be desirable to use to which the working electrodes are mounted on one side and the counter electrode is mounted to the other side.

In an embodiment of the invention (not shown), counter electrode 28 and reference electrode 34 may be a single, uniform electrode or may be a single electrode having a first region functioning as a counter electrode and a second region functioning as a reference electrode.

Housing 12 is preferably formed from a solid cylinder of polyethylene such that cavity 14 may be easily formed by drilling through the cylinder. As should be clear, however, the particular form or configuration of the housing or arrangement and configuration of the electrodes can be altered to suit the final instrument package into which the electrochemical cell is to be adapted.

Figure 3:
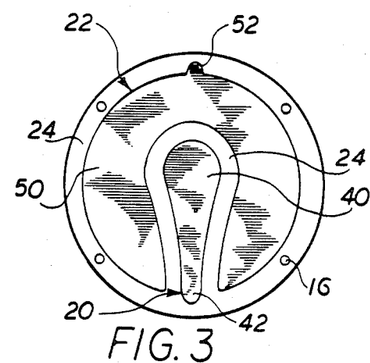
FIG. 3 is a section along I—I of FIG. 2 showing the first and second working electrodes bonded to a common membrane.

Referring to FIG. 3, first working electrode 20 includes a gas diffusion membrane 24 having a catalytic portion 40 bonded thereto that is electrochemically reactive with noxious gases, such as ethylene oxide. Membrane 24 is preferably a Zitex or Goretex porous fluorocarbon membrane. Other membrane materials may be used provided such materials have characteristics similar to Zitex and Goretex, including not becoming wetted by the liquid electrolyte, having a large number of pores (e.g., 50% porous) which in turn have a small pore size, being thin enough to avoid restricting the concentration of the noxious gas being measured and being nonreactive with that noxious gas and liquid electrolyte. Preferably first working electrode 20 is prepared by mixing a suitable catalyst 40 with a polytetrafluorethylene (Teflon) dispersion and painting the mixture onto gas diffusion membrane 24. The membrane and catalyst are dried and sintered to provide a good bond. Catalytic portion 40 is preferably selected from the group consisting of palladium, platinum, iridium, ruthenium, rhodium, osmium, and alloys and mixtures of these materals with gold. Most preferably, catalyst 40 is iridium and more specifically iridium black. Catalytic portion 40 also includes a tab 42 to which is electrically connected lead 31 shown in FIG. 2.

Still referring to FIG. 3, second working electrode 22 is in juxtaposition to first working electrode 20 and, preferably, essentially surrounds first working electrode 20. Second working electrode 22 is of such a shape and/or so positioned that it is, preferably, not exposed to the environmental or ambient air drawn into cell 10 through inlet 34. Second working electrode 22 may be any electrode that has electrochemical activity with reaction products, preferably oxidation or reduction products, produced at the first working electrode. Preferably, second working electrode 22 includes a gas diffusion membrane, preferably the same membrane 24 used with first working electrode 22, and a catalytic portion 50. More preferably the membrane is made of Zitex or Goretex material, and the catalytic portion 50 is selected from the same group described for the first working electrode, preferaby being iridium and more specifically iridium black. Second working electrode 22 is preferably manufactured in a similar manner to first working electrode 20. Catalytic portion 50 also includes a tab 52 to which is electrically connected lead 33 shown in FIG. 2.

Part of the problem related to the use of an electrochemical cell for the measurement of noxious gases, such as ethylene oxide, may be due to the nature of the oxidation/reduction reaction that occurs with regard to the electrochemical detection and measurement of the noxious gas. More specifically, during the electrochemical sensing process of ethylene oxide, ethylene oxide is believed to be oxidized and/or hydrolyzed to a variety of different compounds, including acetylene, formaldehyde, methanol, ethylene glycol, oxalic acid and carbon monoxide. Not only would such possible oxidation/hydrolysis products of ethylene oxide cause sensitivity and measurement problems with respect to ethylene oxide, they would tend to poison the electrodes and in turn, drastically shorten the measurement life of the cell to the point that a sensor using an electrochemical cell would not be commercially attractive. Second working electrode 22 is believed to act as a scavenger electrode which further oxidizes the byproducts from the oxidation/reduction of ethylene oxide or other measured noxious gases occurring at the first working electrode. In this manner, poisoning of the first working electrode 20 is minimized permitting good sensitivity and an extended useful life of the electrochemical cell.

Figure 4:
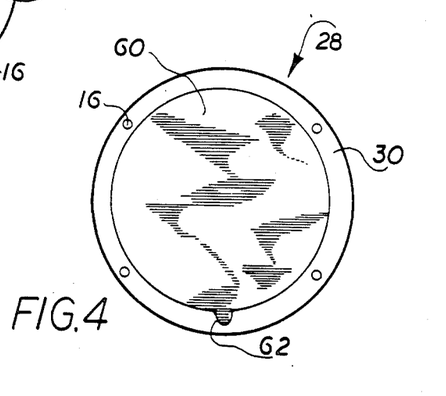
FIG. 4 is a section along II—II of FIG. 2 showing the counter electrode bonded to a membrane.

Referring to FIG. 4, counter electrode 28 may be any material at which oxidation or reduction occurs without limiting the oxidation/reduction reaction occurring at the first working electrode. Counter electrode 28 preferably includes a gas diffusion membrane 30 and a catalytic portion 60. More preferably, the counter electrode 28 is also made from a Zitex or Goretex material, and the catalyst portion 60 is selected from the same group of catalysts discussed for the first working electrode. Most preferably, the catalyst portion is platinum, and more specifically, platinum black. Counter electrode 28 is preferably manufactured with a catalyst portion bonded thereto in the same manner as first working electrode 20 is manufactured. Catalytic portion 60 has a tab 62 to which is electrically connected lead 37 shown in FIG. 2.

Most preferably, first working electrode 20 and second working electrode 22 are so positioned in housing 12 so that catalytic portions 40 and 50 face catalytic portion 60 of counter electrode 28.

Now referring to FIGS. 1, 2 and 5, reference electrode 34 may be any suitable electrode which will operate with the cell and will be stable in cell environment. Suitable reference electrodes include a normal hydrogen electrode, a saturated calomel electrode, a silver/silver chloride electrode, a glass or pH electrode, a mercury/mercury sulfate electrode and a quinhydrone electrode. Preferably, reference electrode 34 is a quinhydrone electrode and most preferably is a 50:50 chloranil/graphite electrode.

In a further embodiment, reference electrode 34 is coated with a material which is ionically conductive when in contact with the electrolyte. This improves its stability. Suitable materials include sodium sulfate intimately mixed with semi-solid gel materials, such as agar or carbosil or with plastics, such as polycarbonate. In a most preferred embodiment, reference electrode 24 is a 50:50 chloranil/graphite electrode coated with an intimate mixture of synetic rubber or polycarbonate powder and sodium sulfate. Reference electrode 34 has a tab 72 to which lead 39 is electrically connected.

The electrolyte EL may be any suitable aqueous, non-aqueous or solid electrolyte which does not react with the electrode at the cell operating potentials and which is capable of supporting ion flow between the first working electrode and the counter electrode, the variety and extent of such electrolytes being within the knowledge of one skilled in the art. The electrolyte and solvent (if any is used) should also exhibit a sufficiently high enough breakdown potential to remain stable and inert at the operating potentials of the cell. Suitable electrolytes include inorganic and organic salts, such as perchloric acid or potassium chloride dissolved in water or in non-aqueous solvents, such as propylene carbonate, dimethylsulfoxide, dimethylformamide, and $\gamma$-butyrolactone. Suitable solid electrolytes include solid ionic polymers bathed in water, such as perfluorosulfonic acid (Nafion) and perflurocarboxylic acid. The preferred liquid electrolyte is an aqueous electrolyte, with the most preferred electrolyte being an aqueous solution of sulfuric acid.

An important requirement in the preferred electrochemical cell and method of the present inventon is the simultaneous maintenance of a fixed potential between first working electrode 20 and reference electrode 34 and between second working electrode 22 and reference electrode 34, the fixed potential on second working electrode 22 being maintained at a voltage higher than the fixed potential being maintained on first working electrode 20. This dual constant potential maintenance of the electrochemical cell of the invention is accomplished by the use of a suitable potential maintenance means, and preferably by the use of two potentiostats or a bipotentiostat connected to the cell in the manner depicted in the circuit diagram of FIG. 6. The potentials being maintained should be independent of the concentration of the ethylene oxide or other noxious gas to be detected. Potentiostats and bipotentiostats are known in the art and operate to maintain a constant relative potential between two electrodes.

In the most preferred cell of the present invention, a fixed potential is maintained on the first working electrode relative to the reference electrode of from about 1.0 to 1.8, preferably between 1.4 and 1.6, volts with respect to the potential of the reversible hydrogen couple in the electrolyte of the cell. Also, a fixed potential is simultaneously maintained on the second working electrode relative to the reference electrode of from about 1.0 to 2.2, preferably 1.5 to 2.0, volts with respect to the potential of the reversible hydrogen couple in the electrolyte of the cell.

In other embodiments of the electrochemical cell of the invention, the potential maintenance means may be as simple as a resistor or resistors connected between the working and counter electrodes, or the potential may be maintained by appropriate selection of the working and reference electrodes to electrochemically potentiostat the cell.

The scavenger electrode 22 is a second working electrode suited to oxidize or reduce byproducts of the first oxidation or reduction reaction. The energy which is required for the oxidation or reduction can be supplied as a constant potential to the electrode as described above. However, a constant current-controlled, second working (scavenger) electrode can be employed resulting in the advantage that the current between the working and reference electrodes may be maintained. Maintenance of constant current through the second electrode may result in the cell being less sensitive to vibration and movement, and to overall drift. By maintaining the current at the second working (scavenger) electrode, the potential shift at the first working electrode will be minimized. The current may be maintained between about 1 mA and 30 mA depending on cell geometry.

The electrochemical cell of the present invention is preferably connected to means for continuously measuring the current flowing between the first working electrode and the counter electrode, the current measured being a measure of the concentration of ethylene oxide or other noxious gas being detected.

The electrochemical cell of the present invention provides a generally linear response in measuring the noxious gas. With ethylene oxide, the response is from about 0.05 to 100 parts per million ethylene oxide in about 10 to 100 seconds to 90% of the final value. Typically, the cell of the present invention provides a 3 to 5 uA/ppm output response. Further, the electrochemical cell has an operating temperature range of 0° to 40° C. and preferably 10° to 35° C.

Figure 6:
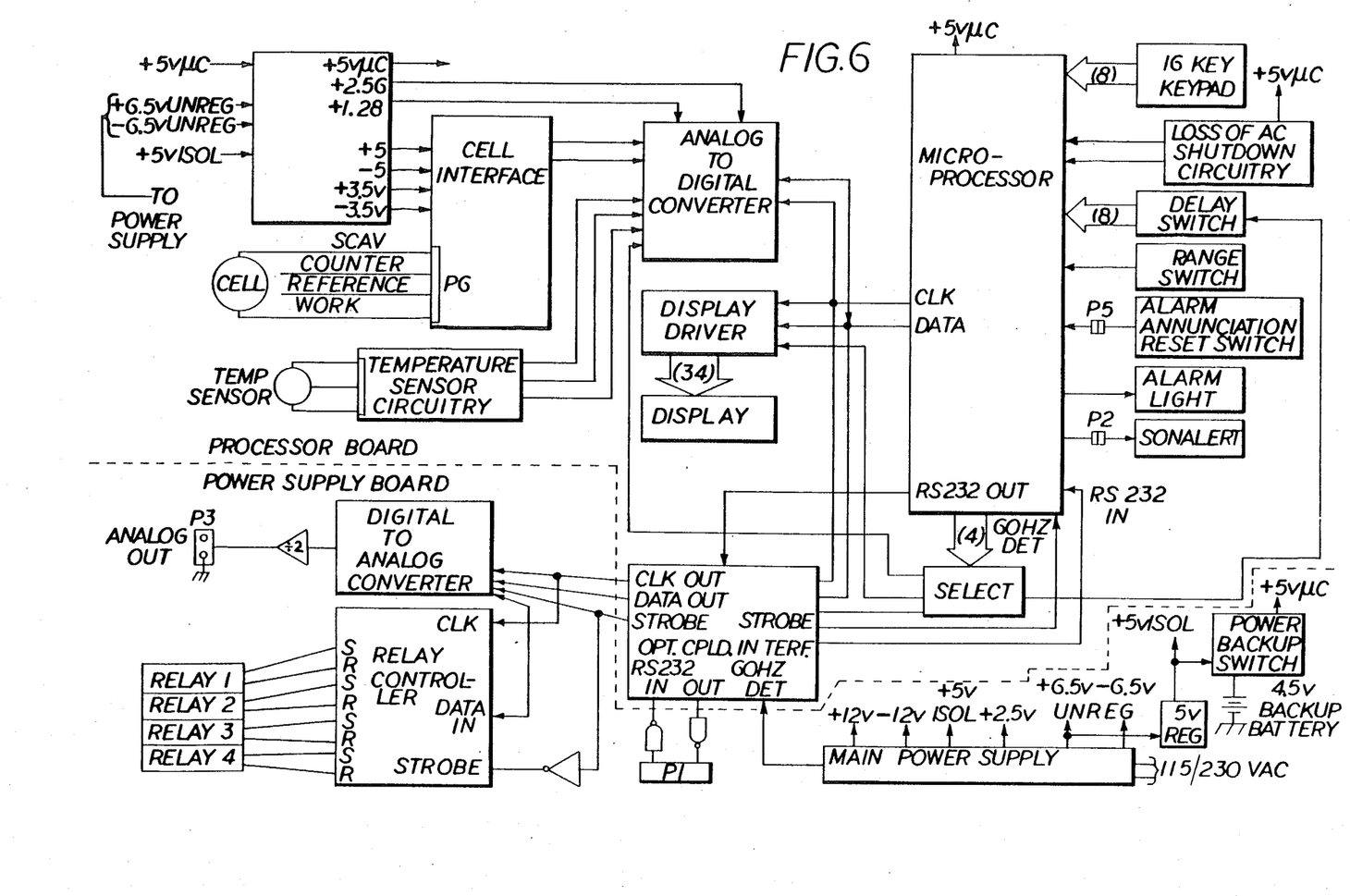
FIG. 6 is a block diagram of a circuit useful in detecting and measuring a noxious gas with the cell of the present invention.

FIG. 6 depicts a block diagram of a circuit useful with the electrochemical cell of the invention as illustrated in FIGS. 1, 2 and 5. The analog portion of the circuit maintains well regulated DC voltages of +5 V, −5 V, +1.23 V, −1.23 V, +3.5 V, +0.1 V, and +2.56 V, supplies the cell with tightly regulated DC voltages of +400 mV on the scavenger electrode, −700 mV on the reference electrode and 0 V on the working electrode, offsets the resting current of approximately 3 ua from the cell by means of a variable current source on the working electrode and converts the working electrode current to a voltage suitable to drive the analog to digital converter. This stage has two switchable ranges, one corresponding to a full scale output equivalent to 10 ppm and the other to a full scale output equivalent to 100 ppm. The analog portion also converts the ouput voltage from the preceding stage to an 8 bit digital word for the microprocessor through an analog to digital converter and measures the temperature environment and feeds the analog to digital converter with a temperature proportional voltage.

The digital portion of the circuit is controlled by a microprocessor and accepts keyput inputs to calibrate and set the alarm point, detects if the 60 Hz power supply is interrupted and allows processor memory backup with loss of power, displays alarm setting and concentration of gas on a liquid crystal display, announces an alarm condition with a flashing light, sound device, and activated relays and causes an analog DC voltage proportional to gas concentration for external recording or measuring purpose with a maximum of 1.0 V to appear on an output amplifier.

The power supply shown in the circuit contains transformer isolated, regulated DC supplies of +12 V, −12 V, +5 V and +2.5 V. The supply will accept either 115 or 230 V AC input selectable by switch. It also contains a relay controller, four relays for controlling external devices, a digital to analog converter for generating an output voltage proportional to the gas concentration and an RS232 interface for communication with compatible external devices. A memory backup battery is included to supply the microprocessor memory with enough current to store critical software parameters. A power switch is also included to turn the sensor pump on and off.

EXAMPLES

An electrochemical cell in accordance with the present invention was constructed and tested as follows:

EXAMPLE 1

Sintering of Porous Gas Electrodes

Powdered metal catalysts (iridium, platinum) are mixed with Teflon dispersion (TFE30, Dupont) and painted onto a porous Teflon (either Goretex, W. L. Gore & Co., or Zitex, Chemplast). The electrodes are dried for 7 minutes at 98° C. and then transferred to another oven and sintered for 11 minutes at 300°-330° C.

Preparation of Chloranil Reference Electrode

Approximately 2 grams of a 50:50 chloranil/graphite mixture which has been ball milled for 24 hours is pressed into a 0.340×0.5120 inch pellet at 4000 lbs. of pressure for ½-1 minute. Before pressing, a coiled Hastalloy wire is placed in the chloranil/graphite mixture as a current collecting lead.

A mixture of 3 grams polycarbonate powder (Mobay Chemical Co. Type 5200) and 6-9 grams sodium sulfate ($Na_2SO_4$, Baker, Reagent Grade), finely ground, were mixed in 10 ml dichloromethane (Practical Grade). The above-described pellets are coated with this mixture and air dried for 24 hours. The pellet is then soaked for 1-2 days in the electrolyte of choice.

Alternatively, a mixture of 30 ml of a commercial thermal plastic synthetic rubber (Plastic-Dip, PDI Inc.) and 20 grams of finely ground sodium sulfate ($NA_2SO_4$, Reagent Grade) were mixed with 5 ml of a solvent (1,1,1 Trichloroethane). The above-described pellets are coated with this mixture and air dried for 24 hours. The pellet is then soaked for 1-2 days in the electrolyte of choice.

Description of Cell Manufacture and Testing

An electrochemical cell was made and tested for response to ethylene oxide in the following manner. 110 mg of iridium black (as supplied by Alpha-Ventron) was mixed with 150 ml of Dupont TFE dispersion T30 diluted 4 ml to 15 ml deionized water. The mixture was spread evenly across a Zitex porous Teflon membrane and sintered. Two working electrodes were manufactured in this manner. These working electrodes were positioned in a cell fixture with a platinum counter electrode manufactured similarily with platinum black (obtained from Englehard Industries) and with a chloranil/graphite reference electrode. A high concentration (12N) sulfuric acid was used as the electrolyte. After potentiostating both working electrodes ($E_1 = +750$ mV, $E_2 = +1.1$ V vs chloranil) for one week, the base currents were measured. Ethylene oxide was introduced to the front of the cell at a measured flow/rate (300 cc/min). The current output at $E_1$ was equal to 5 uA/ppm ethylene oxide. The ethylene oxide was mixed with air and the linearity of the cell was about 90% over 0 to 20 ppm ethylene oxide. This cell was tested weekly. The output stabilized at about 3 uA/ppm and the base current stabilized at about 5 uA. After a period of several weeks, base currents began to substantially increase. The potential of the cell was moved cathodic at 50 mV increments until the base current was close to the original base current. Cell testing continued in this manner for 5 months.

EXAMPLE 2

Another cell was made similarily to the first cell described in Example 1. However, the reference electrode, chloranil/graphite, was coated in a mix of sodium sulfate and polycarbonate resin with dichloromethane as a solvent. The pellet was air dried and then soaked for one week in sulfuric acid. This reference electrode was placed in the cell and the cell was exposed to ethylene oxide. The base currents and response was similar to that described for the original cell. After several weeks, no increase in base current was noted. The cell was tested successfully with no change in potential for four months.

Table I presented below lists the common interferants to the measurement of ethylene oxide by the electrochemical cell of the invention and the concentration of each such interferants equivalent to one part per million ethylene oxide. Care must be taken to account for any such interferants in the measuring environment when the electrochemical cell of the present invention is used.

TABLE 1

Interference Test Data

| Gas EtO | PPM Concentration Equivalent to 1 PPM |
|---|---|
| Carbon dioxide | No interference at 4% |
| Carbon monoxide | 160 |
| Freon | No interference at 100% |
| Isopropanol | 3 |
| Formaldehyde | 0.2 |
| Nitrous Oxide | No interference at 5% |
| Nitrogen | No interference at 80% |
| Acetone | 100 |
| Ethanol | 2 |

EXAMPLE 3

Ethanol (ethyl alcohol) was placed in a Metronics Dynacalibrator and 56 ppm of the vapor was introduced to a cell in accordance with the invention. Daily the cell was allowed to equilibrate with the air and the base current was measured. The remainder of the time the cell was continuously exposed to ethanol vapors. Two cells were tested for the ability to continuously oxidize ethanol. The first cell was a standard three-electrode (a first working electrode, a counter electrode and a reference electrode) cell with an iridium black first working electrode, a platinum counter electrode and chloranil reference electrode. The potential of the working electrode was held at +700 mV vs. chloranil. The second cell was the three electrode cell just described but with an additional working electrode of iridium black held at 1.1 V vs. chloranil.

After one week on test, the base current of the cell with a second working (scavenger) electrode had not changed appreciably, while the base current of the three electrode cell had increased slightly, 1.8 uA to 2.2 uA or about 22% over the test period. It is expected that a continuous ethanol exposure would eventually poison the three-electrode sensor, but that the four-electrode sensor would operate for a much longer time period.

EXAMPLE 4

As in Example 3, three electrode and four electrode cells were exposed to ethylene glycol vapors for one week in a similar manner. The cell performance without use of the scavenger electrode was generally poorer than the cell with a scavenger maintained at 1.1 V vs. chloranil. In particular, cell outputs decayed about 40% over the week without use of the scavenger electrode. The outputs of the cell with the scavenger decayed 20-25% over the same time period but this could be attributed to normal cell aging. After both cells were left to recover on an air purge for 96 hours, the cell with the scavenger electrode recovered its original zero current, whereas the cell without the scavenger electrode did not recover. The cell span currents did not recover in either cell, which is attributed to normal cell aging.

EXAMPLE 5

The performance of a cell may be judged by its ability to maintain within a reasonable degree the initial zero and span currents after a continuous long exposure to a test gas. In the case of ethylene oxide, the performance of a three electrode cell degraded seriously. With the addition of a fourth electrode, the cell performance was judged acceptable. In order to extend the use of the scavenger electrode to other gases, long term exposure of the cell to other test gases was evaluated. Ethylene glycol and ethanol were tested and compared to ethylene oxide. A summary of the results are presented below.

| Test Gas | S zero i. | S zero f. | NS zero i. | NS zero f. | S span i. | S span f. | NS span i. | NS span f. |
|---|---|---|---|---|---|---|---|---|
| Ethylene Oxide (100 ppm) | 1.0 uA | 6.0 uA 500% | 1.5 uA | 70 uA 4567% | 154 uA | 70 uA 55% | 223 uA | 75 uA 66% |
| Ethylene Glycol (2.2 ppm) | 6.2 uA | 10 uA 60% | 5.4 uA | 20 uA 270% | 68 uA | 44 uA 35% | 51 uA | 30 uA 41% |
| Ethanol (56 ppm) | 8.0 uA | 8.5 uA 6% | 7.5 uA | 9.5 uA 27% | 39 uA | 32 uA 18% | 28 uA | 22 uA 21% |

S: Scavenger electrode
NS: No scavenger electrode
i: Initial current
f: Final current As the summary indicates, a four electrode cell with a scavenger electrode could be advantageously used in the measurement of ethylene glycol and ethanol.

Although the invention has been described in detail for the purposes of illustration, it is to be understood that such detail is solely for that purpose and that variations can be made therein by those skilled in the art without departing from the spirit and scope of the invention except as it may be limited by the claims.

What is claimed is:

1. An electrochemical cell for quantitatively detecting ethylene oxide comprising:
   (a) a first working electrode comprising a gas diffusion membrane having bonded thereto a catalytic portion electrochemically reactive with ethylene oxide;
   (b) a second working electrode having electrochemical activity with oxidation/reduction products produced at the first working electrode;
   (c) a counter electrode;
   (d) a reference electrode;
   (e) an electrolyte in contact with the catalytic portion of the first working electrode and in contact with the second working, counter and reference electrodes;
   (f) means for containing said electrolyte and said first and second working electrodes, said counter electrode and said reference electrode;
   (g) means for maintaining a fixed potential on said first working electrode relative to said reference electrode of from above 1.0 to about 1.8 volts with respect to the potential of the reversible hydrogen couple in the electrolyte of the cell; and
   (h) means for maintaining a fixed potential on said second working electrode relative to said reference electrode of from about 1.0 to 2.2 volts with respect to the potential of the reversible hydrogen couple in the electrolyte of the cell, the fixed potential on said second working electrode being maintained at a voltage higher than the fixed potential being maintained on said first working electrode.

2. The electrochemical cell of claim 1 wherein said counter and reference electrodes are a single electrode.

3. The electrochemical cell of claim 1 wherein the catalytic portion of the first working electrode is selected from the group consisting of palladium, platinum, iridium, ruthenium, rhodium, osmium and mixtures thereof with gold.

4. The electrochemical cell of claim 3 wherein the catalytic portion of the first working electrode is iridium black.

5. The electrochemical cell of claim 1 wherein the second working electrode is a gas diffusion membrane having bonded thereto a catalytic portion selected from the group consisting of palladium,, platinum, iridium, ruthenium, rhodium, osmium and mixtures thereof with gold.

6. The electrochemical cell of claim 5 wherein the catalytic portion of the second working electrode is iridium black.

7. The electrochemical cell of claim 1 wherein the counter electrode is a gas diffusion membrane having bonded thereto a catalytic portion selected from the group consisting of palladium, platinum, iridium, ruthenium, rhodium, osmium and mixtures thereof.

8. The electrochemical cell of claim 7 wherein the catalytic portion of the counter electrode is platinum black.

9. The electrochemical cell of claim 1 wherein the electrolyte is selected from the group consisting of aqueous electrolytes, non-aqueous electrolytes and solid electrolytes that remain stable and inert during operation of the cell.

10. The electrochemical cell of claim 9 wherein the aqueous electrolyte is an aqueous solution of sulfuric acid.

11. The electrochemical cell of claim 10 wherein the reference electrode is selected from the group consisting of a normal hydrogen electrode, a saturated calomel electrode, a silver/silver chloride electrode, a glass pH electrode, a mercury/mercury sulfate electrode, and a quinhydrone electrode.

12. The electrochemical cell of claim 1 wherein the reference electrode is a chloranil/graphite electrode coated with an intimate mixture of polycarbonate or synthetic rubber and sodium sulfate.

13. The electrochemical cell of claim 1 wherein said means for containing the electrolyte and the electrodes comprise a housing having an electrolyte receiving cavity coextensively positioned therethrough and end plates sealingly mounted at opposite ends of said housing.

14. The electrochemical cell of claim 1 wherein the first working electrode, the second working electrode and the counter electrode are made from a porous fluorocarbon material.

15. The electrochemical cell of claim 1 further including
(i) means for continuously measuring current flow between the first working electrode and the counter electrode of the cell, said measured current being a measure of the concentration of ethylene oxide being detected.

16. The electrochemical cell of claim 1 wherein said means for maintaining a fixed potential on said first working electrode relative to said reference electrode is a potentiostat.

17. The electrochemical cell of claim 1 wherein said means for maintaining a fixed potential on said second working electrode relative to said reference electrode is a potentiostat.

18. The electrochemical cell of claim 1 wherein the reference electrode is a chloranil/graphite electrode.

19. An electrochemical cell for quantitatively detecting ethylene oxide comprising:
(a) a first working electrode comprising a gas diffusion membrane having bonded thereto a catalytic portion electrochemically reactive with ethylene oxide;
(b) a second working electrode having electrochemical activity with oxidation/reduction products produced at the first working electrode;
(c) a counter electrode;
(d) a reference electrode;
(e) an electrolyte in contact with the catalytic portion of the first working electrode and in contact with the second working, counter and reference electrodes;
(f) means for containing said electrolyte and said first and second working electrodes, said counter electrode and said reference electrode;
(g) means for maintaining a fixed potential on said first working electrode relative to said reference electrode of from about 1.0 to 1.8 volts with respect to the potential of the reversible hydrogen couple in the electrolyte of the cell; and
(h) means for maintaining a fixed current through said second working electrode of from about 1 mA to 30 mA.

* * * * *

UNITED STATES PATENT AND TRADEMARK OFFICE
CERTIFICATE OF CORRECTION

PATENT NO.   :  4,707,242

DATED        :  November 17, 1987

INVENTOR(S)  :  Alan A. Schneider, et al.

It is certified that error appears in the above-identified patent and that said Letters Patent is hereby corrected as shown below:

Column 2, line 51, the term "second electrode" should read -- second working electrode -- .

Column 6, line 42, the phrase "oxidation or reduction should read -- oxidation or reduction reaction --.

Column 6, line 48, the phrase "through the second" should read -- through the second working -- .

Column 7, line 25, the word "keyput" should read -- keypad -- .

Signed and Sealed this

Twenty-eighth Day of June, 1988

Attest:

DONALD J. QUIGG

*Attesting Officer*　　　　　*Commissioner of Patents and Trademarks*

UNITED STATES PATENT AND TRADEMARK OFFICE
CERTIFICATE OF CORRECTION

PATENT NO. : 4,707,242
DATED : November 17, 1987
INVENTOR(S) : Alan A. Schneider, et al.

It is certified that error appears in the above-identified patent and that said Letters Patent is hereby corrected as shown below:

In Claim 1, at column 10, line 62, change the phrase "from above 1.0 to about 1.8 volts" to -- from about 1.0 to 1.8 volts -- .

In Claim 1, at column 10, line 67, change the phrase "from about 1.0 to 2.2 volts" to -- from above 1.0 to about 2.2 volts -- .

Signed and Sealed this

Twenty-second Day of November, 1988

Attest:

DONALD J. QUIGG

Attesting Officer      Commissioner of Patents and Trademarks